United States Patent
Lee et al.

(10) Patent No.: US 8,580,741 B2
(45) Date of Patent: Nov. 12, 2013

(54) COSMETIC COMPOSITIONS FOR SKIN-TIGHTENING AND METHOD OF SKIN-TIGHTENING USING THE SAME

(75) Inventors: Kye-Ho Lee, Seoul (KR); Sung-Ho Chung, Seoul (KR); Ji-Hoon Song, Seoul (KR); Jin-Sung Yoon, Seoul (KR); Ji-Hyun Lee, Seoul (KR); Moon-Ju Jung, Seoul (KR); Jong-Hwan Kim, Gunpo (KR)

(73) Assignee: STC Nara Co., Ltd., Cheonan (KR)

( * ) Notice: Subject to any disclaimer, the term of this patent is extended or adjusted under 35 U.S.C. 154(b) by 878 days.

(21) Appl. No.: 12/522,401

(22) PCT Filed: Jan. 11, 2007

(86) PCT No.: PCT/KR2007/000199
§ 371 (c)(1),
(2), (4) Date: Jan. 18, 2010

(87) PCT Pub. No.: WO2008/084890
PCT Pub. Date: Jul. 17, 2008

(65) Prior Publication Data
US 2010/0125048 A1    May 20, 2010

(30) Foreign Application Priority Data
Jan. 8, 2007 (KR) .................. 10-2007-0001883

(51) Int. Cl.
*A61K 38/00* (2006.01)
*A61K 38/14* (2006.01)
*A61P 17/00* (2006.01)

(52) U.S. Cl.
USPC ............... 514/18.6; 514/18.8; 514/20.9

(58) Field of Classification Search
None
See application file for complete search history.

(56) References Cited

U.S. PATENT DOCUMENTS

| 7,022,668 B2 | 4/2006 | Parente Duena et al. |
| 2003/0147830 A1 * | 8/2003 | Phillips et al. ............. 424/70.14 |

FOREIGN PATENT DOCUMENTS

| CN | 1259043 | 7/2000 |
| CN | 1822770 | 8/2006 |
| EP | 0533408 | * 3/1993 |
| JP | 10-212226 | 8/1998 |
| JP | 2002-516263 | 6/2002 |
| JP | 2002-516838 | 6/2002 |
| JP | 2004-075572 | 3/2004 |
| JP | 2004-182687 | 7/2004 |
| JP | 2004-331578 | 11/2004 |
| JP | 2004-534023 | 11/2004 |
| JP | 2004-534076 | 11/2004 |
| JP | 2005-516048 | 6/2005 |
| JP | 2007-519722 | 7/2007 |
| WO | 98/44904 | 10/1998 |
| WO | 2005/013708 | 2/2005 |

* cited by examiner

*Primary Examiner* — Noble Jarrell
(74) *Attorney, Agent, or Firm* — Lexyoume IP Meister, PLLC.

(57) ABSTRACT

The present invention relates to a skin-tightening cosmetic composition and a method of applying the same, and more specifically, to a cosmetic composition a method of applying the same that includes a hydrolyzed plant protein and glycoprotein. The cosmetic composition includes a hydrolyzed plant protein and glycoprotein in an optimal amount, thereby causing the occurrence of an immediate contraction effect and a long-lasting contracting effect, and achieving skin improvements such as skin moisturizing and induction of synthesizing collagen and elastine in use of the composition over a long period of time.

12 Claims, 1 Drawing Sheet

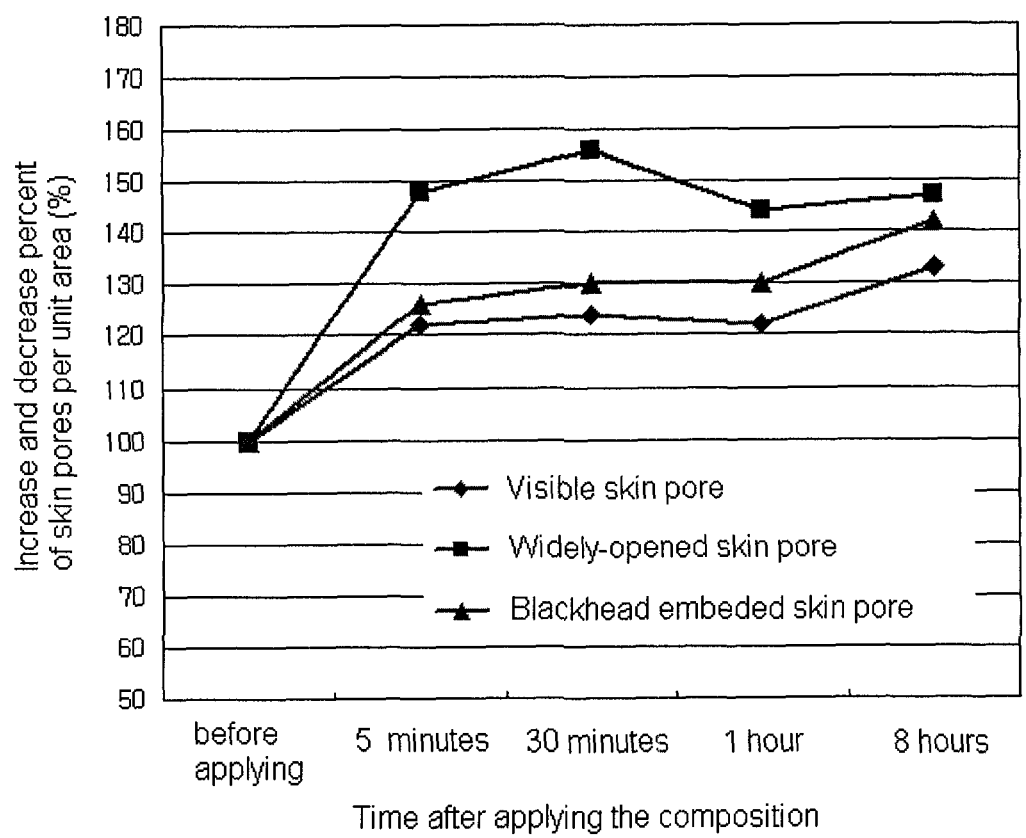

COSMETIC COMPOSITIONS FOR SKIN-TIGHTENING AND METHOD OF SKIN-TIGHTENING USING THE SAME

CROSS-REFERENCE TO RELATED APPLICATION

This application claims priority to and the benefit of Korean Patent Application No. 10-2007-0001883 filed in the Korean Intellectual Property Office on Jan. 8, 2007, the entire contents of which are incorporated herein by reference.

BACKGROUND OF THE INVENTION (a) Field of the Invention

The present invention relates to a skin-tightening cosmetic composition and a method of applying the same, and more specifically, to a skin-tightening cosmetic composition and a method of applying the same that provides an occurrence of an immediate contraction effect and a long-lasting contracting effect, and that achieves skin improvements such as skin moisturizing and induction of synthesizing collagen and elastine in use of the composition over a long period of time.

(b) Description of the Related Art

Aging of skin is divided into intrinsic aging and extrinsic aging. Intrinsic aging is a natural process in which a content of extracellular elastine fiber is reduced in the extracellular matrix due to the degradation of elastine fiber. Extrinsic aging is a phenomenon of change in function or appearance of skin due to the repetitive exposure to sunlight (photo-aging), environmental pollution, and stress.

When a human being is aged 18 years or above, intrinsic aging proceeds and is accelerated depending on the extent of the extrinsic aging. As the skin ages, skin elasticity is gradually reduced, and particularly the skin of the face sags seriously and the asymmetry extent between right and left sides of the face increases more and more.

In general, moisturizing or wrinkle-declining cosmetics are used for preventing skin aging and improving skin elasticity. Conventional cosmetics have been used for the purpose of only preventing skin aging, but have a difficulty in improvement in skin elasticity and skin contraction in a short time.

SUMMARY OF THE INVENTION

To resolve the problems of the prior art, the object of the present invention is to provide a skin-tightening cosmetic composition that causes immediate skin contraction and a long-lasting contracting effect. In addition, when the cosmetic composition is used for a long time, skin improvements such as skin moisturizing and induction of synthesizing collagen and elastine are achieved.

Another object of the present invention is to provide a method of tightening skin including a step of applying the cosmetic composition to a skin region in need.

BRIEF DESCRIPTION OF THE DRAWINGS

FIG. 1 is a graph showing the increase and decrease percent of "visible skin pores" (skin pores with a mean area), "widely-opened skin pores" (skin pores with more than a mean area), and "blackhead embedded skin pores" (skin pores with a darker color than mean color) per unit area of skin with the passage of time.

DETAILED DESCRIPTION OF THE PREFERRED EMBODIMENTS

These and other objects of the invention will be more fully understood from the following description of the invention, the referenced drawings attached hereto, and the claims appended hereto.

The present invention relates to a skin-tightening cosmetic composition including a hydrolyzed plant protein having a weight average molecular weight (Mw) of 200,000 to 600,000 in an amount of 10 to 30 parts by weight, and a glycoprotein in an amount of 0.01 to 10 parts by weight.

Preferably, the hydrolyzed plant protein is at least one selected from the group consisting of hydrolyzed wheat protein, hydrolyzed barley protein, hydrolyzed oat protein, and hydrolyzed soy protein.

The glycoprotein is preferably Pseudoalteromonas Antarctica NF3.

The composition further contains at least an organometallic compound selected from the group consisting of copper gluconate, zinc gluconate, magnesium gluconate, and magnesium aspartate in an amount of 0.01 to 10 parts by weight based on 100 parts by weight of the composition.

In addition, the present invention relates to a method of tightening skin including a step of applying the cosmetic composition to a skin region in need.

The present invention will now be described in more detail.

While researching a cosmetic composition for tightening skin, the present inventors found that when a hydrolyzed plant protein and a glycoprotein are combined to the cosmetic composition in an optimal amount, the composition provides an immediate contraction effect and a long-lasting effect. In addition, the present inventors found that when the cosmetic composition is used for a long time, it provides skin improvements such as skin moisturizing and induction of synthesizing collagen and elastine, and thus they completed the present invention based on the foundation.

The skin-tightening cosmetic composition of the present invention includes hydrolyzed plant protein and glycoprotein.

The hydrolyzed plant protein is generally added to cosmetic compositions as a skin-conditioning agent or to mascara, and to hair gel as a hair-styling agent for making a hair style elastic and bulky.

The hydrolyzed plant protein imparts immediate contraction and forms a protective film to prevent moisture evaporation.

The hydrolyzed plant protein is at least one selected from the group consisting of hydrolyzed wheat protein, hydrolyzed barley protein, hydrolyzed oat protein, and hydrolyzed soy protein, and is more preferably hydrolyzed wheat protein.

The hydrolyzed plant protein is obtained by hydrolyzing the plant protein with an enzyme according to the convention preparation method, or is commercially available.

The hydrolyzed plant protein has a weight average molecular weight (Mw) of 200,000 to 600,000, more preferably 300,000 to 500,000, and most preferably 500,000. That is, to achieve at least a skin-tightening sensation, the weight average molecular weight of the hydrolyzed plant protein is preferably 200,000 or higher, and to prevent a bad feeling due to a sticky property of the cosmetic composition, the weight average molecular weight is preferably 600,000 or lower.

The hydrolyzed plant protein is added to the cosmetic composition in an amount of 10 to 30 parts by weight. That is, to achieve minimal skin-contraction, the amount of hydrolyzed plant protein is 10 parts by weight or higher, and to prevent the viscosity from increasing excessively and the feeling deterioration in use of the cosmetic composition, the amount is 30 parts by weight or lower, preferably, based on 100 parts by weight of the composition.

The glycoprotein recovers damaged skin by stimulating cell growth, and is preferably Pseudoalteromonas Antarctica NF3.

The Pseudoalteromonas Antarctica NF3 is a glycoprotein that is secreted from Pseudoalteromonas Antarctica to survive at the South Pole. The glycoprotein prevents skin drying and protects skin epidermis.

The amount of glycoprotein can be determined in considering the effect, and is preferably 0.01 to 10 parts by weight based on 100 parts by weight of the composition.

By including the hydrolyzed plant protein and the glycoprotein in a suitable mixing ratio in the cosmetic composition of the present invention, immediate contraction of skin and maintenance of the effect are achieved due to the synergic effect of the two components. Accordingly, when using the cosmetic composition over the long term, it provides skin moisture, and induction of synthesis of collagen and elastine. Thus, it has an advantage of a notable improvement in skin.

In addition, the cosmetic composition further includes an organometallic compound.

Organometallic compounds stimulate synthesis of pyruvic acid by activating the metabolism of the materials in skin, and induce synthesis of proteins such as collagen and elastine. The exemplary organometallic compound is at least one selected from the group consisting of copper gluconate, zinc gluconate, magnesium gluconate, and magnesium aspartate.

The amount of the organometallic compound can be selected in consideration of the effect required for the cosmetic composition of the present invention, and is preferably is 0.01 to 10 parts by weight based on 100 parts by weight of the composition.

In addition, the cosmetic composition further includes at least additives selected from the group consisting of a moisturizing agent, a chelating agent, an antiseptic agent, an emollient, and a thickening agent.

The additives can be selected from the conventional additives in the art, and thus the kind and content are not particularly defined.

Preferably, the moisturizing agent is at least one selected from the group consisting of butylene glycol and glycerin, in an amount of 0.001 to 10.0 parts by weight. The chelating agent is ethylene diamine tetraacetic acid (EDTA) in an amount of 0.001 to 0.2 parts by weight based on 100 parts by weight of the composition. The emollient is contained in an amount of 0.01 to 0.1 parts by weight based on 100 parts by weight of the composition. The thickening agent can be contained depending on the form of the cosmetic composition, and is contained in an amount of 0.01 to 1.0 parts by weight based on 100 parts by weight of the composition.

The cosmetic composition of the present invention is prepared in various forms depending on the mixing ratio of the components. Preferably, the composition can be formed in toner, serum, lotion, cream, and mask.

In addition, the present invention provides a method of tightening skin including a step of applying the cosmetic composition.

Preferably, the method of tightening skin includes a step of applying 0.01 to 1.0 g of the cosmetic composition to a skin region in need, for example the cheek, forehead, eye rims, nose, etc. The cosmetic composition includes a hydrolyzed plant protein having a weight average molecular weight (Mw) of 200,000 to 600,000 in an amount of 10 to 30 parts by weight, and a glycoprotein in an amount of 0.01 to 10 parts by weight based on 100 parts by weight of the composition.

As the cosmetic composition is applied, the subject feels a skin-tightening sensation on applied region at 1 to 5 minutes after applying, and the contracted skin effect is visible.

The present invention is further explained in more detail with reference to the following examples. These examples, however, should not be interpreted as limiting the scope of the present invention in any manner.

Examples 1 to 4

The components indicated in Table 1 were mixed and formed as a serum (Example 1), a lotion (Example 2), a cream (Example 3), and a mask (Example 4), respectively.

TABLE 1

| Components | Example 1 | Example 2 | Example 3 | Example 4 |
|---|---|---|---|---|
| *Hydrolyzed Wheat Protein (Mw = 500,000) | 10.0 | 10.0 | 10.0 | 10.0 |
| Pseudoalteromonas Antarctica NF3 | 0.1 | 0.1 | 0.1 | 0.1 |
| *Organometallic Compound | 0.02 | 0.02 | 0.02 | 0.02 |
| Glycerin | 1.5 | 1.5 | 1.5 | 1.5 |
| Butylene Glycol | 3.0 | 3.0 | 3.0 | 1.0 |
| Disodium EDTA | 1.5 | 2.5 | 2.5 | 2.5 |
| Squalene | 0.5 | 2.1 | 5.5 | 2.3 |
| Sorbitan Stearate | 0.5 | 1.5 | 1.5 | 1.6 |
| POE (20 mol) Sorbitan Monostearate | 0.001 | 0.001 | 3.5 | 2.5 |
| Deionized water | 82.879 | 79.279 | 72.380 | 78.480 |

*the content is parts by weight
*hydrolyzed wheat protein: (Tritisol XM manufactured by Croda (England))
*organometallic compound: (copper gluconate:zinc gluconate:magnesium aspartate = 1:1:1) (SEPITONIC M3 manufactured by SEPIC)

Examples 5 to 12

Toner Type

The components indicated in Table 2 were mixed and formed as a toner-type cosmetic.

TABLE 2

| | Example (parts by weight) | | | | | | | |
|---|---|---|---|---|---|---|---|---|
| Components | 5 | 6 | 7 | 8 | 9 | 10 | 11 | 12 |
| *Hydrolyzed Wheat Protein (Mw = 500,000) | 10 | 10 | 10 | 30 | 30 | 30 | 30 | 30 |
| Pseudoalteromonas Antarctica NF3 | 0.01 | 10 | 0.1 | 0.1 | 0.01 | 0.01 | 10 | 10 |
| *Organometallic Compound (SEPITONIC M3) | 0.5 | 0.5 | — | 10 | 0.01 | 10 | 0.01 | 10 |
| Butylene glycol | 3.0 | 3.0 | 3.0 | 3.0 | 3.0 | 3.0 | 3.0 | 3.0 |
| Disodium EDTA | 0.1 | 0.1 | 0.1 | 0.1 | 0.1 | 0.1 | 0.1 | 0.1 |

TABLE 2-continued

| Components | Example (parts by weight) | | | | | | | |
|---|---|---|---|---|---|---|---|---|
| | 5 | 6 | 7 | 8 | 9 | 10 | 11 | 12 |
| Methyl Paraben | 0.15 | 0.15 | 0.15 | 0.15 | 0.15 | 0.15 | 0.15 | 0.15 |
| Deionized Water | 86.24 | 76.25 | 86.65 | 56.65 | 66.73 | 56.74 | 56.74 | 46.75 |

*hydrolyzed wheat protein: (Tritisol XM manufactured by Croda (England))
*organometallic compound: (copper gluconate:zinc gluconate:magnesium aspartate = 1:1:1) (SEPITONIC M3 manufactured by SEPPIC)

Comparative Examples 1 to 8

The components indicated in Table 3 were mixed and formed as a skin type cosmetic. Hydrolyzed wheat proteins having a weight average molecular weight of 100,000, 500,000, or 700,000 were used.

TABLE 3

| Classification | Comparative Example (parts by weight) | | | | | | | |
|---|---|---|---|---|---|---|---|---|
| | 1 | 2 | 3 | 4 | 5 | 6 | 7 | 8 |
| *Hydrolyzed Wheat Protein (Mw = 500,000) | — | 0.1 | 10 | — | — | — | — | 30 |
| *Hydrolyzed Wheat Protein (Mw = 100,000) | 10 | — | — | 30 | — | — | — | — |
| *Hydrolyzed Wheat Protein (Mw = 700,000) | — | — | — | — | 10 | 30 | — | — |
| *Pseudoalteromonas Antarctica* NF3 | — | 0.01 | — | 0.01 | — | 10 | — | — |
| *Organometallic Compound (SEPITONIC M3) | — | 0.01 | — | — | 0.01 | — | 10 | — |
| Butylene Glycol | 3.0 | 3.0 | 3.0 | 3.0 | 3.0 | 3.0 | 3.0 | 3.0 |
| Disodium EDTA | 0.1 | 0.1 | 0.1 | 0.1 | 0.1 | 0.1 | 0.1 | 0.1 |
| Methyl Paraben | 0.15 | 0.15 | 0.15 | 0.15 | 0.15 | 0.15 | 0.15 | 0.15 |
| Deionized Water | 86.75 | 96.63 | 86.75 | 66.74 | 86.74 | 56.75 | 86.75 | 66.75 |

*hydrolyzed wheat protein: (Tritisol XM manufactured by Croda (England))
*organometallic compound: (copper gluconate:zinc gluconate:magnesium aspartate = 1:1:1) (SEPITONIC M3 manufactured by SEPPIC)

Test Example 1

To evaluate the skin contraction effect of the cosmetic compositions obtained from Examples 5 to 12 and Comparative Examples 1 to 8, sensory evaluations were carried out as follows.

Sixty four (64) women aged 21 to 40 were divided into eight (8) test groups having eight (8) members each. The test groups washed on their faces, and uniformly applied the cosmetic composition to their cheek, forehead, eye rims, nose, etc. at an amount of 0.1 to 0.5 g, respectively. Then, the sensory evaluations were performed for skin moisturizing effect after 8 hours, skin tightening effect after 5 minutes and 8 hours, skin irritating effect, and skin feeling, and the results are represented in Table 4 (Examples 5~12) and Table 5 (Comparative Examples 1~8).

The skin feeling was measured by 6 grades where an excellent skin feeling is given a mark of 5 points, and no skin feeling is given a mark of 0 points. No skin irritating effect and a good skin feeling effect are graded at 0 points, and a serious skin irritating effect and a bad skin feeling effect are graded at 5 points.

TABLE 4

| Valuation items | Example (parts by weight) | | | | | | | |
|---|---|---|---|---|---|---|---|---|
| | 5 | 6 | 7 | 8 | 9 | 10 | 11 | 12 |
| Skin moisture effect | 2.7 | 3.1 | 3.3 | 3.7 | 3.8 | 3.5 | 3.4 | 4.1 |
| Skin tightening effect (5 minutes after applying) | 2.1 | 2.3 | 2.1 | 4.5 | 4.6 | 4.7 | 4.7 | 4.7 |
| Skin tightening effect (8 hours after applying) | 3.5 | 3.8 | 3.5 | 4.1 | 4.0 | 4.4 | 4.7 | 4.7 |
| Skin irritating effect | 0.0 | 0.0 | 0.0 | 0.0 | 0.0 | 0.0 | 0.0 | 0.0 |
| Skin feeling | 0.8 | 0.7 | 0.6 | 1.1 | 0.9 | 1.1 | 1.3 | 0.9 |

TABLE 5

| Valuation items | Comparative Example (parts by weight) | | | | | | | |
|---|---|---|---|---|---|---|---|---|
| | 1 | 2 | 3 | 4 | 5 | 6 | 7 | 8 |
| Skin moisturizing effect | 0.7 | 0.8 | 1.7 | 0.8 | 0.8 | 1.4 | 1.7 | 1.9 |
| Skin tightening effect (5 minutes after applying) | 0.1 | 0.3 | 2.2 | 0.1 | 2.7 | 3.8 | 0.8 | 3.3 |
| Skin tightening effect (8 hours after applying) | 0.7 | 0.4 | 2.5 | 0.1 | 2.8 | 3.6 | 0.4 | 3.5 |
| Skin irritating effect | 0.1 | 0.1 | 0.1 | 0.1 | 0.0 | 0.1 | 0.1 | 0.0 |
| Skin feeling | 0.7 | 0.9 | 1.2 | 0.9 | 2.3 | 4.6 | 0.8 | 0.9 |

As shown in Tables 4 and 5, the compositions of Examples 5 to 12 showed occurrence of immediate skin contraction after 5 minutes and maintenance of the effect even after 8 hours with no skin irritating effect and an excellent moisturizing effect. On the other hand, the compositions of Comparative Examples 1 to 8 included the hydrolyzed plant protein having weight average molecular weights out of the suitable ranges or that did not comprise the glycoprotein, and thus the skin tightening effect, skin moisturizing effect, and skin feeling were deteriorated. Although the compositions of Comparative Examples 5 and 6 showed a good skin tightening effect due to hydrolyzed wheat protein having a weight average molecular weight of 700,000, the bad skin feelings such as an airtight feeling and a sticky feeling were deteriorated.

Test Example 2

The extent of skin contraction with the passage of time was measured for the cosmetic compositions of Examples 6, 7, and 10.

"Extent of skin contraction" was indirectly determined by measuring the increase and decrease of the number of skin pores per unit area of skin. That is, the number of skin pores per unit area was indicated as a constant value. If the number of skin pores increase after applying the cosmetic composition, it means that the skin pores come near each other due to the skin contraction.

Specifically, 11 subjects were selected from the subjects for Test Example 2 and uniformly applied to their cheek the cosmetic compositions of Examples 6, 7, and 10 at an amount of 0.1 to 0.5 g after washing their faces. Then, the increase and decrease percent of the number of skin pores were measured with the passage of time.

The number of skin pores per unit area was measured with ROBO Skin Analyzer CS50 manufactured by INFORWARD. INC. The front, left, and right sides of the face were photographed while irradiating UV light to the face. Then the skin pores were classified to three groups of "visible skin pores" (skin pores with a mean area), "widely-opened skin pores" (skin pores with more than the mean area), and "blackhead embedded skin pores" (skin pores with a darker color than a mean color) to obtain the increase and decrease percent of skin pores.

The increase and decrease percent of skin pores were calculated on the basis of 100% before applying the cosmetic composition to the cheek, and mean values of the 11 subjects are represented in Table 6 and FIG. 1.

TABLE 6

| Classification | Increase and decrease percent of the number of skin pore (%) | | | | | |
| --- | --- | --- | --- | --- | --- | --- |
| | Before applying | 5 minutes after applying | 30 minutes after applying | 1 hour after applying | 8 hours after applying | mean |
| Visible skin pores | 100 | 122 | 124 | 122 | 133 | 125 |
| Widely-opened skin pores | 100 | 148 | 156 | 144 | 147 | 149 |
| Blackhead embedded skin pores | 100 | 126 | 130 | 130 | 142 | 132 |

As shown Table 6, after applying the cosmetic compositions of Examples 6, 7, and 10, the increase and decrease percent of the number of skin pores per unit area rose, which showed the skin contraction of the cosmetic compositions.

As described above, the skin-tightening cosmetic composition of the present invention including a hydrolyzed plant protein and a glycoprotein in a suitable amount causes an immediate contraction effect in use for skin. In addition, when the cosmetic composition is used for a long time, skin improvements such as skin moisturizing and induction of synthesizing collagen and elastine are achieved.

What is claimed is:

1. A skin-tightening cosmetic composition comprising a hydrolyzed plant protein having a weight average molecular weight (Mw) of 200,000 to 600,000 in an amount of 10 to 30 parts by weight, and a glycoprotein in an amount of 0.01 to 10 parts by weight based on 100 parts by weight of the composition, wherein the glycoprotein is Pseudoalteromonas Antarctica NF3.

2. The cosmetic composition according to claim 1, wherein the hydrolyzed plant protein is at least one selected from the group consisting of hydrolyzed wheat protein, hydrolyzed barley protein, hydrolyzed oat protein, and hydrolyzed soy protein.

3. The cosmetic composition according to claim 1, wherein the composition further comprises at least an organometallic compound selected from the group consisting of copper gluconate, zinc gluconate, magnesium gluconate, and magnesium aspartate in an amount of 0.01 to 10 parts by weight based on 100 parts by weight of the composition.

4. The cosmetic composition according to claim 1, wherein the composition further comprises at least an additive material selected from the group consisting of a wetting agent, a chelating agent, an antiseptic, a softener, and a thickening agent.

5. The cosmetic composition according to claim 1, wherein the composition is in a dosage form of toner-type, an serum, lotion, cream, and mask.

6. A method of tightening skin comprising a step of applying the cosmetic composition of claim 5 to a skin region in need.

7. The cosmetic composition according to claim 2, wherein the composition is in a dosage form of toner-type, an serum, lotion, cream, and mask.

8. The cosmetic composition according to claim 3, wherein the composition is in a dosage form of toner-type, an serum, lotion, cream, and mask.

9. The cosmetic composition according to claim 4, wherein the composition is in a dosage form of toner-type, an serum, lotion, cream, and mask.

10. A method of tightening skin comprising a step of applying the cosmetic composition of claim 6 to a skin region in need.

11. A method of tightening skin comprising a step of applying the cosmetic composition of claim 8 to a skin region in need.

12. A method of tightening skin comprising a step of applying the cosmetic composition of claim 9 to a skin region in need.

* * * * *